United States Patent
Bloebaum

[11] Patent Number: 5,876,460
[45] Date of Patent: Mar. 2, 1999

[54] CEMENTED PROSTHETIC COMPONENT AND PLACEMENT METHOD

[76] Inventor: Roy D. Bloebaum, 1643 E. Wasatch Cir., Salt Lake City, Utah 84105

[21] Appl. No.: 709,186

[22] Filed: Sep. 6, 1996

[51] Int. Cl.[6] .................................. A61F 2/30; A61F 2/38
[52] U.S. Cl. .................................................. 623/18; 623/20
[58] Field of Search ................................ 623/16, 18, 19, 623/20, 22, 23, 66; 606/92, 93, 94, 86, 88

[56] References Cited

U.S. PATENT DOCUMENTS

| | | |
|---|---|---|
| 3,774,244 | 11/1973 | Walker . |
| 3,816,855 | 6/1974 | Saleh . |
| 3,837,009 | 9/1974 | Walker . |
| 3,869,731 | 3/1975 | Waugh et al. . |
| 4,285,071 | 8/1981 | Nelson et al. . |
| 4,301,552 | 11/1981 | London . |
| 4,563,778 | 1/1986 | Roche et al. . |
| 4,769,040 | 9/1988 | Wevers . |
| 5,163,963 | 11/1992 | Hewka et al. . |
| 5,171,276 | 12/1992 | Caspari et al. ............................. 623/20 |
| 5,201,768 | 4/1993 | Caspari et al. ............................. 623/20 |
| 5,217,498 | 6/1993 | Henssge et al. . |
| 5,246,459 | 9/1993 | Elias . |
| 5,290,311 | 3/1994 | Baumann . |
| 5,336,266 | 8/1994 | Caspari et al. ............................. 623/20 |
| 5,370,693 | 12/1994 | Kelman et al. . |
| 5,376,124 | 12/1994 | Gustke et al. . |
| 5,480,445 | 1/1996 | Burkinshaw . |

OTHER PUBLICATIONS

A Cement Impactor for Uniform Cement Penetration in the Upper Tibia—Young–Hoo Kim, M.D. P.S. Walker, J. Deland MD Jan.–Feb. 1984 Clinical Orthopaedics & Related Research.

Control of Cement Penetration in Total Knee Arthroplasty P.S. Walker, M. Soudry, F.C. Ewald, & H. Mc Vickar May 1984—Clinical Orthopaedics & Related Research.

*Primary Examiner*—David Isabella
*Attorney, Agent, or Firm*—Kelly Bauersfeld Lowry & Kelley, LLP

[57] ABSTRACT

A prosthetic joint component and related placement method are provided for cemented fixation to a prepared patient bone, with a cement layer and mantle of controlled, predetermined thickness. The prosthetic component, such as a tibial or femoral component for a knee prosthesis, includes an attachment surface with a plurality of spacer pegs protruding therefrom, and bounded by a taller flow restrictor wall which cooperates with the shorter spacer pegs and attachment surface to define an open-sided cavity for receiving a quantity of bone cement. An intruder tool is provided to form a shallow recess in the prepared patient bone for seated reception of the flow restrictor wall on the prosthetic component. The cement cavity of the prosthetic component is filled with bone cement to a height slightly above the spacer pegs and below the flow restrictor wall, whereupon the prosthetic component is placed onto the patient bone with the flow restrictor wall seated within the recess and the spacer pegs contacting the patient bone. During placement of the prosthetic component, the flow restrictor wall prevents lateral escape of the bone cement, resulting in a cement layer and mantle of selected thickness to achieve a substantially optimum strength attachment interface, while preventing cement breakdown at the cement implant interface.

20 Claims, 7 Drawing Sheets

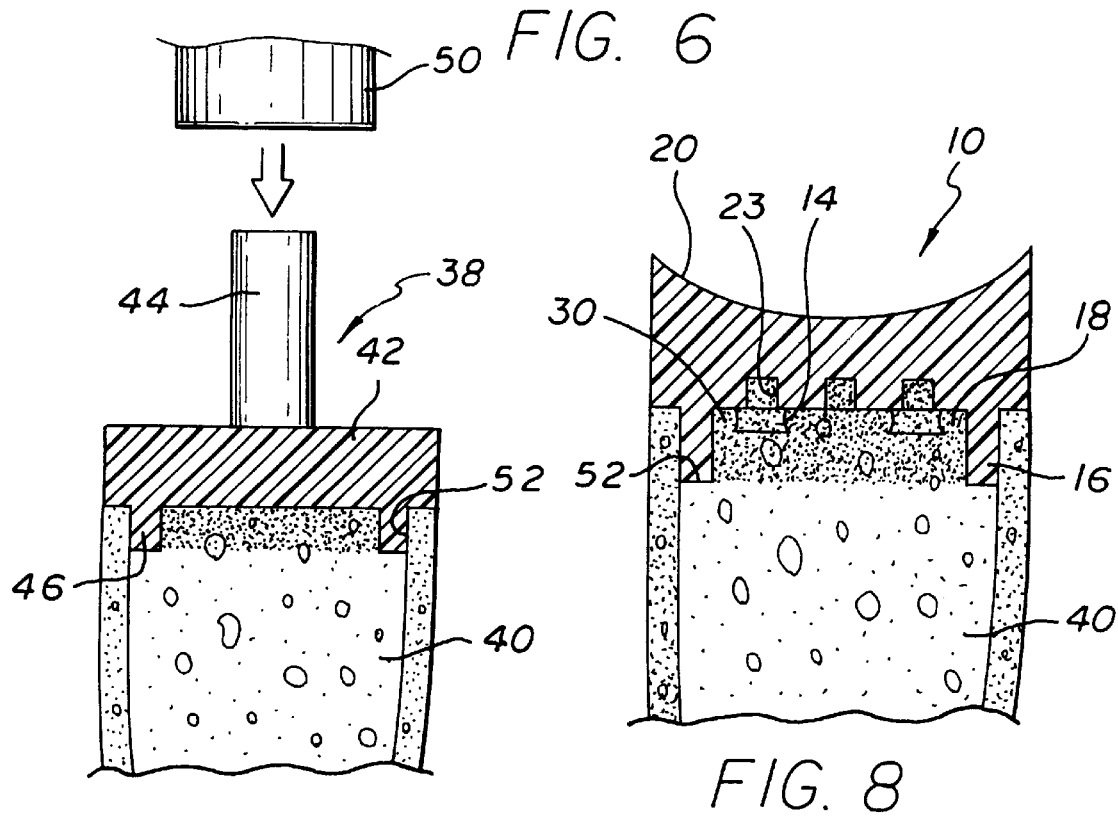
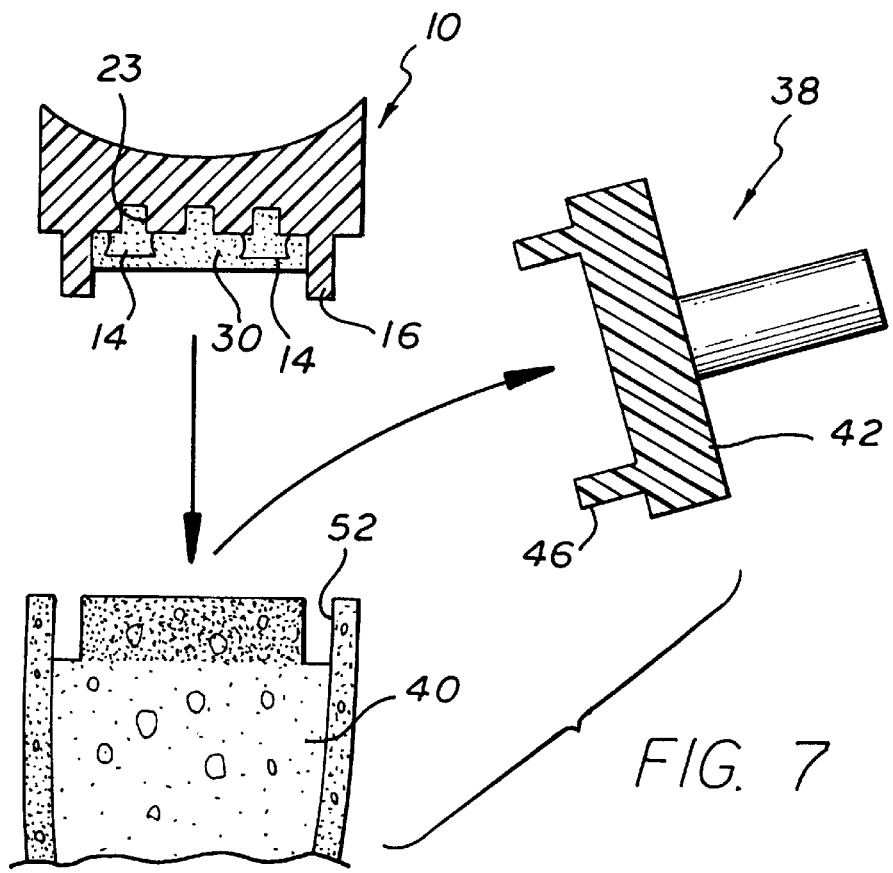

CEMENTED PROSTHETIC COMPONENT AND PLACEMENT METHOD

BACKGROUND OF THE INVENTION

This invention relates generally to improvements in prosthetic devices used for reconstructing human joints, such as a knee joint, hip joint, etc. More particularly, this invention relates to an improved prosthetic component and related method for cemented attachment of the prosthetic component to a prepared patient bone, in a manner achieving a substantially optimum strength attachment interface.

Artificial or prosthetic joint mechanisms for implantation into animals, particularly humans, have been the subject of intensive research and development efforts for many years. Such prosthetic joint mechanisms have typically comprised one or more implant components formed from a relatively biostable material having selected structural properties and a unique shape to replace all or part of a selected anatomical joint, for example, a hip or knee joint. The implant components are installed by surgically accessing the joint and by resection of one or more bone surfaces to accommodate direct attachment thereto of the implant components. One common attachment method has utilized bone cement, such as a methyl methacrylate-based cement or the like used as grouting material to fill up the space between the resected bone surface and the prosthetic component. Alternative attachment methods have relied upon surface coatings of controlled porosity on the prosthetic component in a position to achieve post-operative bone and/or tissue ingrowth.

Although cemented attachment of the prosthetic component can be performed relatively quickly and easily, and does not require a post-operative period during which the strength of the attachment interface is increased (e.g., by bone ingrowth), certain problems and disadvantages exist with respect to cemented components. More specifically, in a typical procedure, bone cement is applied to an attachment surface formed on the prosthetic component, and this attachment surface is then pressed against the prepared patient bone to achieve cemented fixation. However, during such press-on placement, some of the bone cement is normally extruded laterally outwardly from the attachment interface and is lost. Moreover, the prosthetic component can be pressed onto the patient's bone in a slightly cocked or tilted position, so that the thickness of the cement mantle is thicker in some areas and thinner in others. Such nonuniform cement mantle thickness can result in an attachment interface having less than optimum strength, thereby creating an undesired risk of post-operative separation of the prosthetic component from the patient bone.

There exists, therefore, a need for further improvements in prosthetic components of the type adapted for cemented attachment to a prepared patient bone, to provide a cement layer and mantle of controlled and substantially uniform thickness at the attachment interface. The present invention fulfills these needs and provides further related advantages.

SUMMARY OF THE INVENTION

In accordance with the invention, an improved prosthetic component and related placement method are provided for cemented attachment of the prosthetic component to a prepared patient bone, with a cement layer and mantle of controlled and substantially uniform thickness at the attachment interface. The prosthetic component of the present invention is adapted for use in various prosthetic joints, such as a knee joint or hip joint and the like.

The prosthetic component of the present invention includes an attachment surface of selected and typically grooved configuration with a size and shape for substantially mated fit with a resected patient bone. A plurality of spacer pegs having a selected height protrude outwardly from the attachment surface. The attachment surface is bounded by a flow restrictor wall having a selected height greater than the spacer pegs.

An intruder tool is provided for engaging the resected patient bone to form a shallow recess having a size and shape for seated reception of the flow restrictor wall on the prosthetic component. In a preferred form, the intruder tool comprises a base plate with a projecting rim thereon to engage the patient bone and form the shallow recess therein. The base plate and rim of the intruder tool define an open sided cavity which can be used for receiving a quantity of bone cement that can be pressed into porous cancellous bone during the step of forming the shallow recess.

The flow restrictor wall cooperates with the attachment surface of the prosthetic component to define an open-sided cavity for receiving an additional quantity of the bone cement. A leveler tool has a head shaped for mating press-in reception into the prosthetic component cavity to spread the bone cement in a uniform layer to a height at least slightly above the tops of the spacer pegs but below the rim of the flow restrictor wall, with excess bone cement escaping through vent ports formed in the leveler tool head.

The prosthetic component is then press-fitted onto the prepared patient bone, with the flow restrictor wall seated into the shallow recess and the spacer pegs contacting the patient bone. The bone cement contained within the prosthetic component cavity is thus confined by the restrictor wall against escape, for intrusion into the patient bone and further to form a substantially uniform thickness mantle in intimate surface-to-surface contact between the patient bone and the implant prosthesis. A strong, substantially optimum strength cemented attachment interface is thus achieved.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is a fragmented vertical sectional view, taken generally on the line 6—6 of FIG. 5, and illustrating use of the intruder tool;

FIG. 7 is an exploded perspective view illustrating removal of the intruder tool and placement of the prosthetic component, relative to the prepared tibial bone;

FIG. 8 is a fragmented vertical sectional view showing seated placement of the tibial component;

DETAILED DESCRIPTION OF THE PREFERRED EMBODIMENTS

Figure 1:
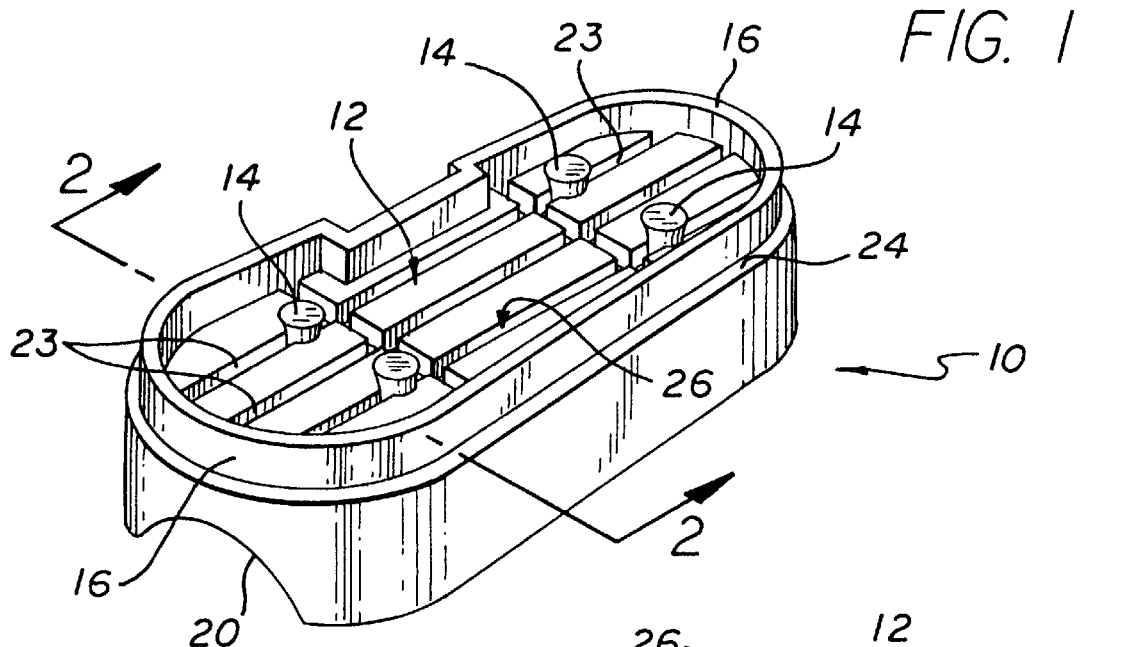
FIG. 1 is a perspective view illustrating an inverted tibial component for a knee prosthesis, constructed in accordance with the novel features of the invention.
Figure 2:
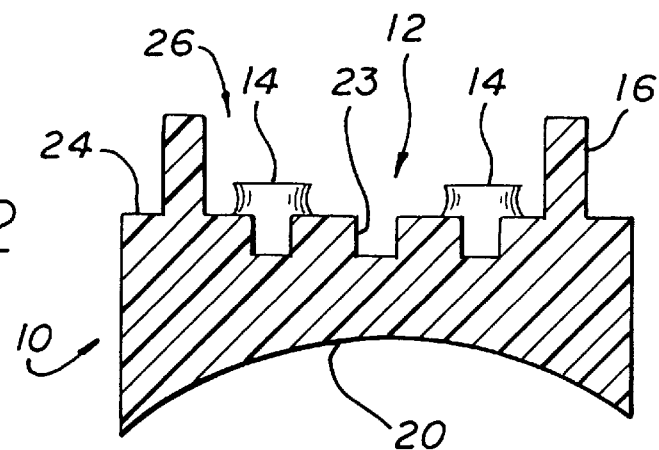
FIG. 2 is a vertical sectional view taken generally on the line 2—2 of FIG. 1.
Figure 3:
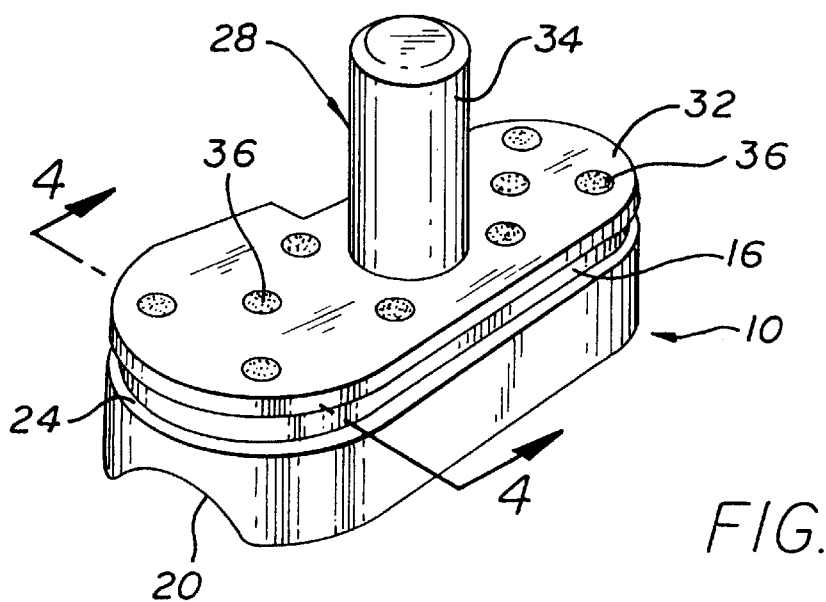
FIG. 3 is a perspective view showing a leveler tool for use in partial filling of an open-sided bone cement cavity defined by the prosthetic component.

As shown in the exemplary drawings, a prosthetic component referred to generally in FIG. 1 by the reference numeral 10 is provided for implantation into the body of a patient, in the course of reconstructing a joint such as a knee joint or hip joint. FIGS. 1–3 show the prosthetic component 10 in the form of a tibial component forming a portion of a knee prosthesis. As shown, the prosthetic component 10 includes an attachment surface 12 for cemented affixation to a prepared patient bone (FIGS. 5–8). The attachment surface 12 is associated with a plurality of relatively short protruding spacer pegs 14 in combination with a surrounding taller flow restrictor wall 16, to achieve an attachment interface defined by a cement layer or mantle 18 (FIG. 8) of controlled and preferably substantially uniform thickness.

Figure 9:
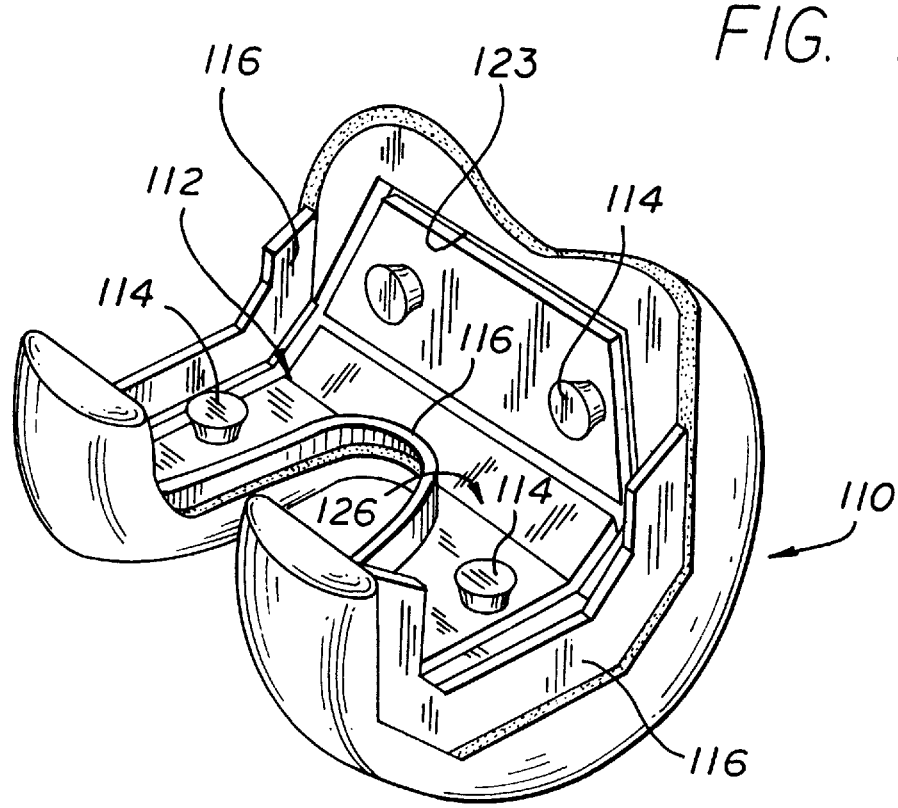
FIG. 9 is a perspective view illustrating a femoral component constructed in accordance with the invention.
Figure 10:
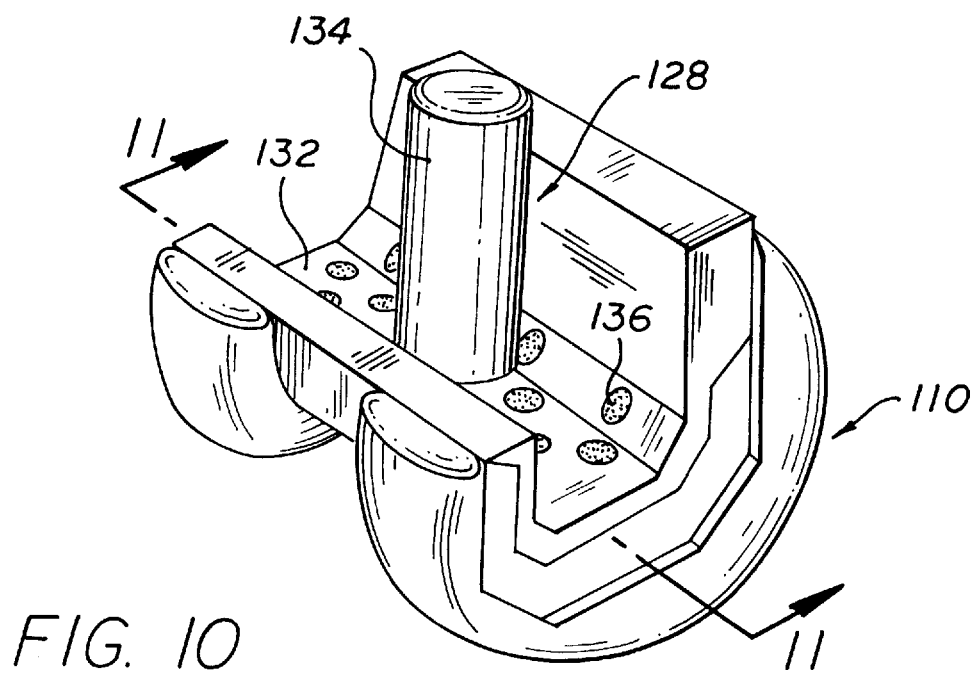
FIG. 10 is a perspective view showing a leveler tool for use in partial filling of an open-sided bone cement cavity defined by the femoral component of FIG. 9.
Figure 11:
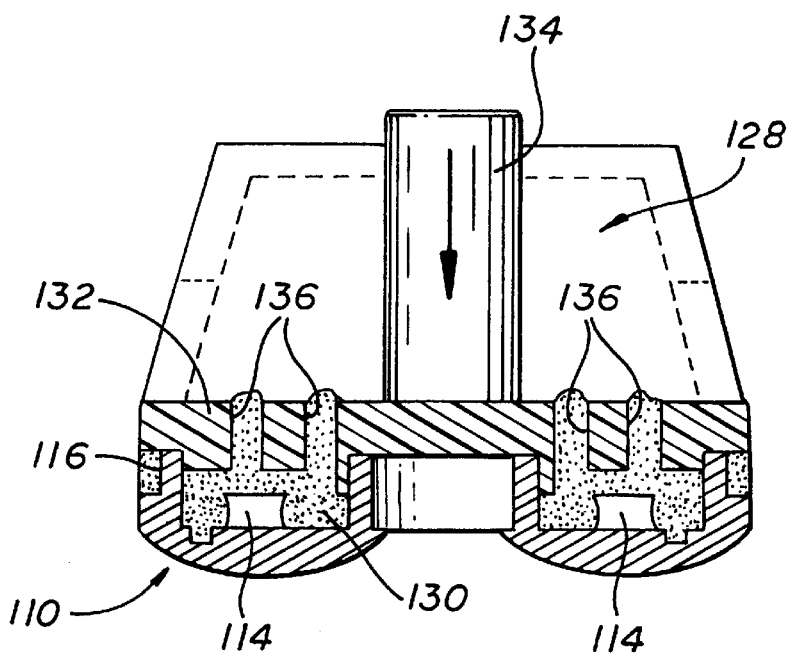
FIG. 11 is a vertical sectional view taken generally on the line 11—11 of FIG. 10.

The tibial prosthetic component 10 is shown in FIGS. 1–3 in an inverted orientation to illustrate construction details of the attachment surface 12 formed on the underside thereof, for subsequent affixation to the upper end of a prepared or resected patient tibia. The illustrative tibial component 10 traditionally provides an upwardly presented bearing member 20 shaped concavely to receive and support the convexly curved condyles of a mated femoral component (shown in FIG. 9). This bearing member 20 is commonly formed from a high density plastic material, such as polyethylene or the like. FIGS. 1–3 show the tibial component 10 having a unitary construction formed from high density plastic material, although it will be understood that the bearing member 20 can be provided as a separate component for assembly with a tibial tray or platform constructed from an alternate material such as titanium or titanium alloy or other suitable biocompatible material, or alternately as a tibial component formed entirely from a suitable biocompatible metal material.

The underside of the tibial component 10 defines the attachment surface 12 which commonly includes an array of shallow, intersecting grooves 23 formed in an otherwise substantially flat or planar surface. The spacer pegs 14 protrude outwardly from this flat surface with a controlled and preferably uniform height. As shown best in FIG. 1, in accordance with a preferred form of the invention, a medial pair and a lateral pair of the spacer pegs 14 are provided, each with a selected anterior posterior spacing. In addition, the spacer pegs 14 have a curved, preferably concave profile shape for enhanced mechanical interlock with bone cement, as will be described in more detail.

The flow restrictor wall 16 surrounds or circumscribes the attachment surface 12 and the spacer pegs 14 protruding therefrom. In the preferred configuration, the flow restrictor wall 16 is inset a short distance from the periphery of the tibial component 10, to define a peripheral land 24 which may be constructed with a roughened surface texture or otherwise formed with a porous bone ingrowth surface. The height of the flow restrictor wall 16 is greater than the height of the spacer pegs 14, as shown best in FIGS. 1 and 2. In one preferred form, the spacer pegs 14 project upwardly from the attachment surface plane by a distance of about two millimeters, whereas the flow restrictor wall 16 projects upwardly from the attachment surface plane by a distance of about six millimeters. The flow restrictor wall 16 cooperates with the spacer pegs 14 and attachment surface 12 to define an open-sided cavity 26 for receiving a quantity of bone cement.

Figure 4:
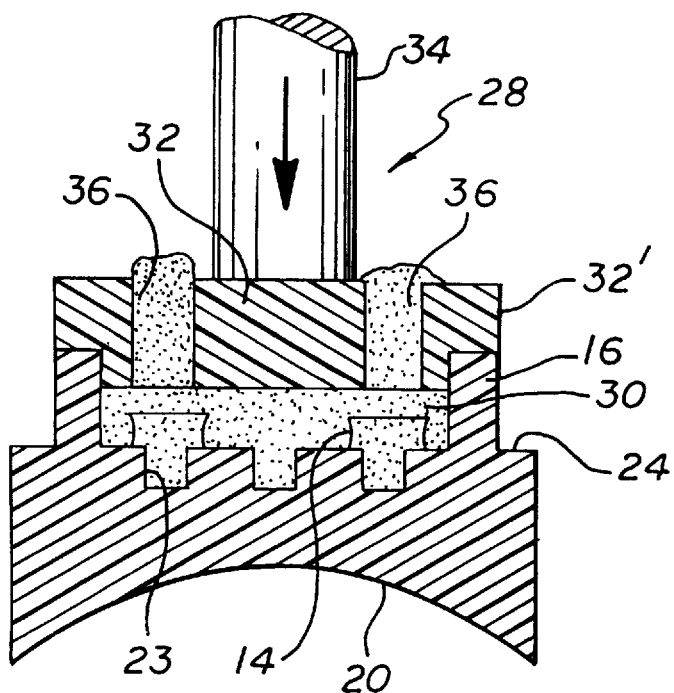
FIG. 4 is a vertical sectional view taken generally on the line 4—4 of FIG. 3.

FIGS. 3 and 4 show a leveler tool 28 for use in partial filling of the bone cement cavity 26 of the tibial component 10 with a quantity of bone cement 30, to a substantially uniform depth. As shown, the leveler tool 28 has a head 32 mounted on a handle 34, wherein the head 32 has a size and shape for slide-fit press-in reception into the bone cement cavity 26 of the tibial component 10. An excess quantity of the bone cement 30 is initially placed into this cavity 26, and the leveler tool 28 is then used to distribute the bone cement 30 to a uniform depth. This distribution step occurs by pressing the tool head 32 into the cavity 26, to spread the bone cement to a uniform depth which is sufficient to cover the spacer pegs 14 but to be below the top of the flow restrictor wall 16. In a preferred configuration, the cement 30 is leveled within the cavity 26 to a depth approximately 2–4 mm above the tops of the pegs 14. FIG. 4 shows the head 32 of the leveler tool 28 pressed partially into the tibial component cavity 26, it being understood that the head 32 is pressed into the cavity 26 until an outer rim 32' engages the top of the flow restrictor well 16. Excess bone cement and air is allowed to escape through a plurality of vent ports 36 formed in the tool head 32.

Figure 5:
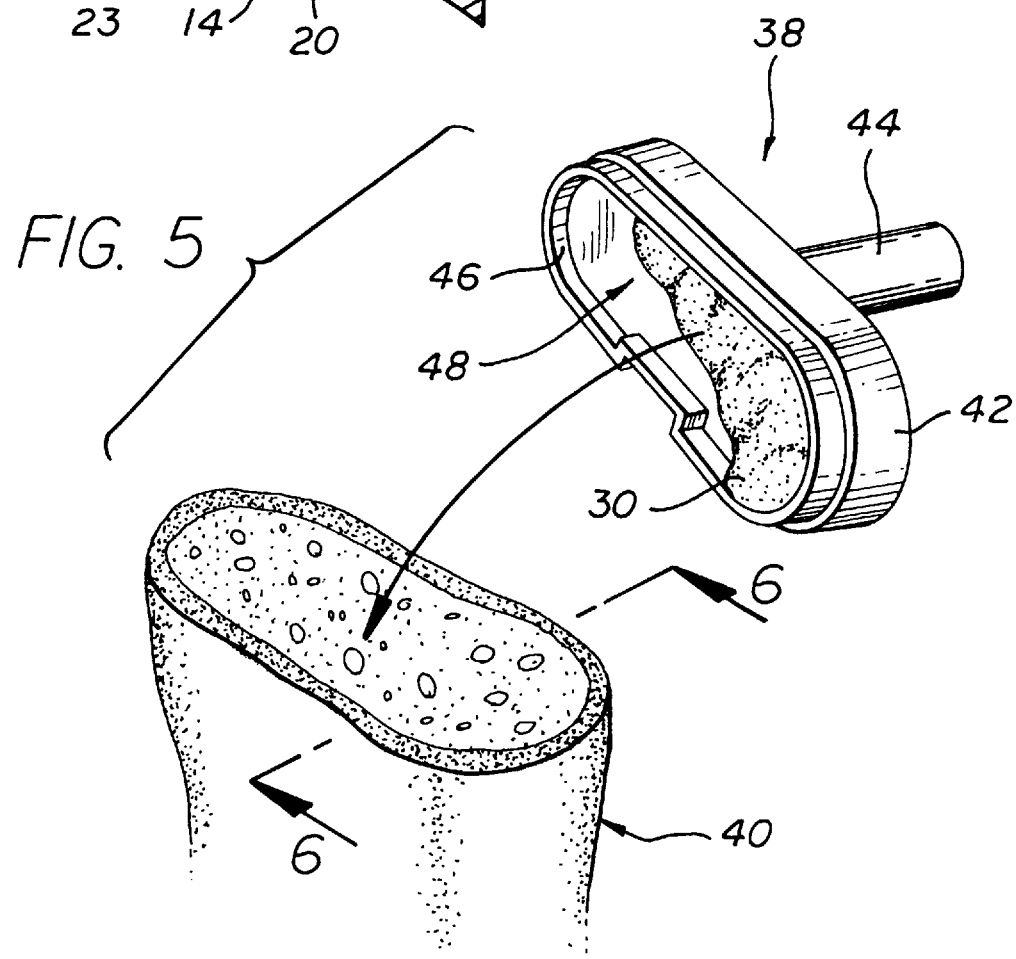
FIG. 5 is an exploded perspective view showing an intruder tool for use in shaping the upper end of a patient tibial bone.

FIGS. 5 and 6 show an intruder tool 38 for use in shaping the upper end of the tibial bone 40 for subsequent cemented placement of the tibial component 10. As shown, the intruder tool 38 has a base plate 42 mounted on a handle 44, with an outwardly projecting cutter rim 46 formed with a configuration conforming to the flow restrictor wall 16 on the prosthetic component 10. The cutter rim 46 has a height, in the preferred form of the invention, corresponding to the difference between the height of the flow restrictor wall 16 and the spacer pegs 14. The cutter rim 46 cooperates with the base plate 42 to define a shallow cavity 48 which may optionally be used for receiving a quantity of the bone cement 30, with FIG. 5 depicting this cavity 48 in a partially filled state so as to illustrate construction details of the base plate 42 and cutter rim 46.

As shown in FIG. 6, the intruder tool 38 is pressed against the partially prepared patient bone 40. An impact tool 50 may be used to drive the intruder tool 38 against the patient bone, so that the cutter rim 46 forms a shallow recess 52 in the prepared patient bone. At the same time, the bone cement 30 carried by the intruder tool 38 is pressed into and fills the porous cancellous bone in the region bounded by the cutter rim 46.

As shown in FIGS. 7 and 8, the intruder tool 38 is then separated from the patient's bone 40, followed by press-on placement of the prosthetic component 10. The prosthetic component 10 is positioned with the flow restrictor wall 16 seated securely into the shallow recess 52, and with the plurality of spacer pegs 14 all firmly contacting the prepared patient bone. In this position, as shown best in FIG. 8, the bone cement 30 is pressed into the porous patient bone to form an interface layer in intimate knitted contact with the bone, and intimately joined to any bone cement previously pressed into the bone by the intruder tool 38. This bone cement 30 is also intimately contacted by the additional bone cement carried by the tibial component 10 in the region surrounding the spacer pegs 14, to define the minimum thickness cement mantle 18. This mantle 18 has a controlled and substantially uniform depth throughout the entire attachment interface. Importantly, the flow restrictor wall 16 cooperates with the mating recess 52 to confine the bone cement 30 against lateral escape, all resulting in a substantially optimized strength attachment.

FIGS. 9–15 show the invention with respect to an alternative prosthetic component, namely, a femoral component 110 for a prosthetic knee joint. The general construction of the femoral component 110 and the related attachment method conform to that previously shown and described with respect to the tibial component 10 depicted in FIGS. 1–8, whereby structures shown in FIGS. 9–15 which are directly analogous to those previously shown and described in FIGS. 1–8 will be identified by common reference numerals increased by 100.

More specifically, the femoral component 110 has a multifaceted geometry for substantially mated fit with a prepared lower end of a patient's femur 140 (FIGS. 12–15). The multifaceted configuration includes an attachment surface 112 with a plurality of upstanding short spacer pegs 114, in combination with a flow restrictor wall 116. Appropriate shallow grooves 123 are normally formed in the attachment surface 112. The spacer pegs 14 have a height which is less than the height of the flow restrictor wall 116. The flow restrictor wall 116 cooperates with the spacer pegs 114 and the attachment surface 112, to define an open-sided cavity 126 for receiving a quantity of bone cement 130 (FIG. 11) that is leveled to a depth above the tops of the spacer pegs 114 by means of a leveler tool 128 (FIGS. 10 and 11) similar to that previously described with respect to the tibial component 10. The leveler tool 128 includes a head 132 having vent ports 136 therein, and a handle 134.

Figure 12:
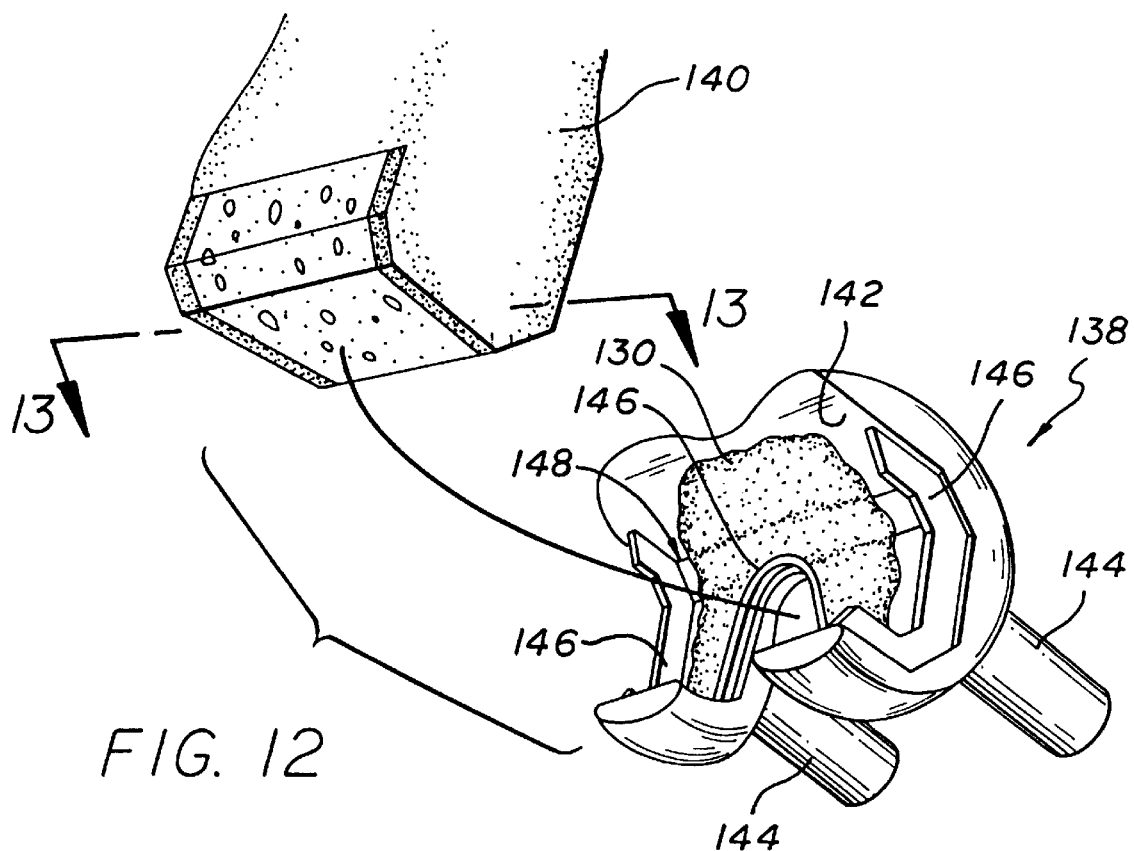
FIG. 12 is an exploded perspective view showing an intruder tool for use in shaping the lower end of a patient femoral bone.
Figure 13:
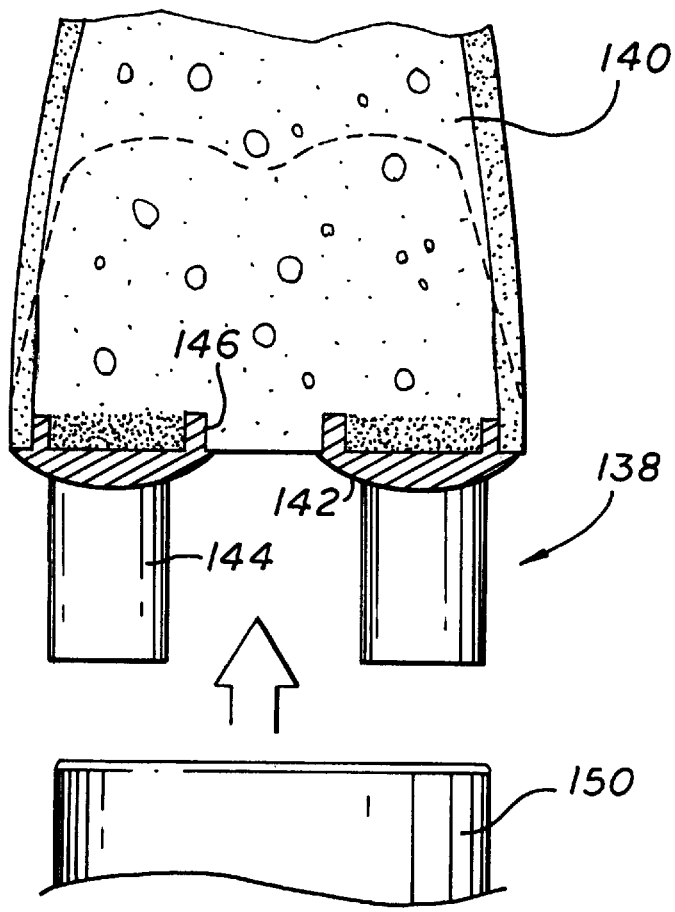
FIG. 13 is a fragmented vertical sectional view taken generally on the line 13—13 of FIG. 12, and illustrating use of the intruder tool.

An intruder tool 138 is provided as shown in FIGS. 12 and 13 for final shaping of the resected femoral bone 140 of the patient. As shown, the intruder tool 138 has a multifaceted base plate 142 mounted on a pair of handles 144, with a short cutter rim 146 protruding from the base plate in a configuration generally conforming to the flow restrictor wall 116 of the femoral component 110. An open-sided cavity 148 is thus defined on the intruder tool 138 which can be used for receiving a quantity of bone cement 130. Once again, the illustrative drawings show the cavity 148 only partially filled with bone cement 130, in order to reveal construction details of the intruder tool. The intruder tool is pressed and may be impacted with a tool 150 (FIG. 13) against the patient bone to form a shallow recess 152, and concurrently to drive the bone cement 130 into the porous cancellous bone.

Figure 15:
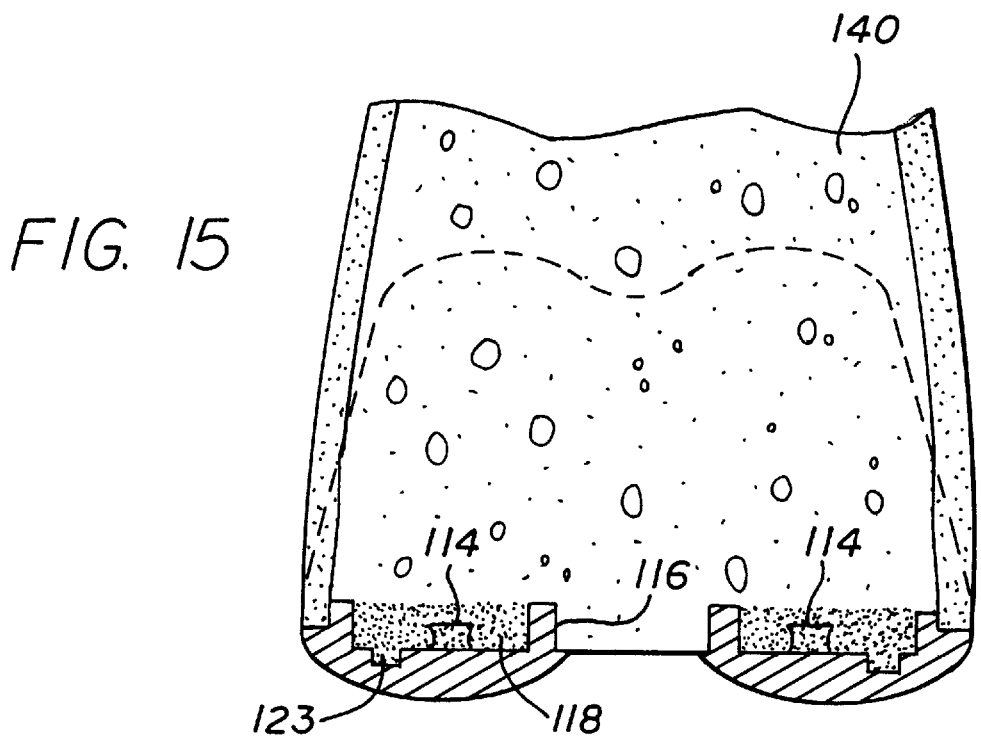
FIG. 15 is a fragmented vertical sectional view showing the femoral component mounted on the prepared patient bone.
Figure 14:
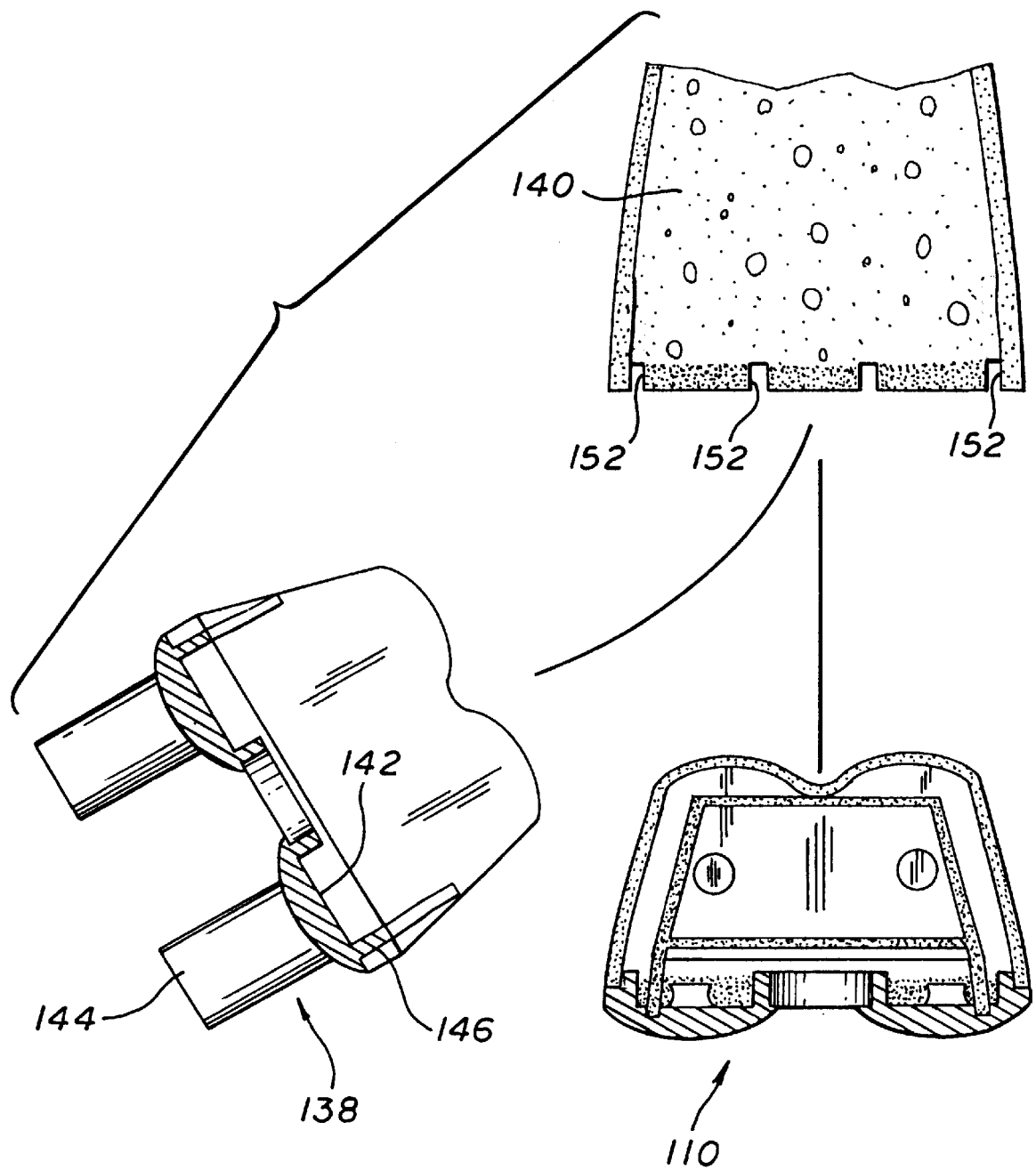
FIG. 14 is an exploded perspective view showing separation of the intruder tool from the femoral bone and placement of the femoral component thereon.

Subsequent removal of the intruder tool (FIG. 14) permits seated placement of the femoral component 110 with bone cement previously placed therein, as viewed in FIGS. 14 and 15. The flow restrictor wall 116 is seated within the formed recess 152, with the spacer pegs 114 contacting the patient bone. As a result, a cement mantle 118 of controlled and preferably uniform thickness is provided across the attachment interface, and in intimate association with any bone cement previously pressed into the cancellous bone. A substantially optimum strength attachment interface results.

A wide variety of further modifications and improvements to the prosthetic component 10 and related attachment method of the present invention will be apparent to persons skilled in the art. In this regard, it will be understood and appreciated that the principles of the invention can be applied to a variety of prosthetic joint components, including patellar implants for knee joints, acetabular cups for hip joints, and other prosthetic devices. Accordingly, no limitation on the invention is intended by way of the foregoing description and accompanying drawings, except as set forth in the appended claims.

What is claimed is:

1. A prosthetic joint component for substantially mated fit with and cemented attachment to a prepared patient bone, said prosthetic joint component comprising:

a prosthetic member defining an attachment surface, at least one spacer peg protruding outwardly from said attachment surface with a selected height, and a flow restrictor wall bounding at least a portion of said attachment surface and having a height greater than the height of said at least one spacer peg;

said attachment surface and said flow restrictor wall cooperatively defining an open-sided cavity for receiving a quantity of bone cement;

said flow restrictor wall having a size and shape for substantially mated fit with the prepared patient bone in a position with said at least one spacer peg contacting the prepared patient bone;

said flow restrictor wall defining means for preventing escape of any substantial portion of the bone cement within said cavity from between said attachment surface and the prepared patient bone when the prosthetic joint component is fitted with the prepared patient bone; and said at least one spacer peg maintaining said attachment surface in predetermined spaced relation with the prepared patient bone when the prosthetic joint component is fitted therewith to form a bone cement mantle of predetermined thickness between said attachment surface and the prepared patient bone.

2. The prosthetic joint component of claim 1 wherein said attachment surface has at least one groove formed therein.

3. The prosthetic joint component of claim 1 wherein said at least one spacer peg comprises a plurality of spacer pegs.

4. The prosthetic joint component of claim 1 wherein said spacer peg has a nonlinear profile shape.

5. The prosthetic joint component of claim 1 wherein said flow restrictor wall circumscribes said attachment surface.

6. A prosthetic joint component and placement system, comprising:

a prosthetic member defining an attachment surface, at least one spacer peg protruding outwardly from said attachment surface with a selected height, and a flow restrictor wall bounding at least a portion of said attachment surface and having a height greater than the height of said at least one spacer peg;

said attachment surface and said flow restrictor wall cooperatively defining an open-sided cavity for receiving a quantity of bone cement;

means for forming a shallow recess in the prepared patient bone, said recess having a size and shape for substantially mated fit reception of said flow restrictor wall, said at least one spacer peg engaging the prepared patient bone when said prosthetic member is fitted with the prepared patient bone with said flow restrictor wall received into said recess; and said flow restrictor wall, when received into said recess, defining means for preventing escape of any substantial portion of the bone cement within said cavity whereby the bone cement forms a mantle between said attachment surface and the prepared patient bone, said mantle having a thickness corresponding substantially to the height of said spacer peg.

7. The system of claim 6 wherein said attachment surface has at least one groove formed therein.

8. The system of claim 6 wherein said at least one spacer peg comprises a plurality of spacer pegs.

9. The system of claim 6 wherein said spacer peg has a nonlinear profile shape.

10. The system of claim 6 wherein said flow restrictor wall circumscribes said attachment surface.

11. The system of claim 6 wherein said recess forming means comprises an intruder tool having a base plate with a cutter rim protruding therefrom for engaging the prepared patient bone to form said recess.

12. The system of claim 6 wherein said recess forming means further includes means for pressing a quantity of bone cement into the prepared patient bone at a location adjacent to said attachment surface when said prosthetic member is fitted with the prepared patient bone.

13. The system of claim 6 further including means for filling said cavity in said prosthetic component with a quantity of bone cement in a layer having a depth at least slightly greater than the height of said spacer peg.

14. The system of claim 13 wherein said filling means comprises a leveler tool having a head for substantially mated sliding reception into said cavity, said head having a plurality of vent ports formed therein.

15. A method of cemented attachment of a prosthetic component to a prepared patient bone, said method comprising the steps of:

forming a prosthetic member with an attachment surface, at least one spacer peg protruding outwardly from the attachment surface with a selected height, and a flow restrictor wall bounding at least a portion of the attachment surface and having a height greater than the height of the spacer peg, whereby the flow restrictor wall and attachment surface cooperatively define an open-sided cavity;

partially filling the cavity in the prosthetic member with a quantity of bone cement in a layer having a thickness at least slightly greater than the height of the spacer peg;

shaping the prepared patient bone for substantially mated fit with the flow restrictor wall of the prosthetic member so that the flow restrictor wall substantially prevents escape of any substantial portion of the bone cement within the cavity when the prosthetic member is fitted with the prepared patient bone; and fitting the prosthetic member with the prepared patient bone with the flow restrictor wall matingly fitting the bone and with the spacer peg contacting the bone, to form a bone cement mantle of predetermined thickness between the attachment surface and the prepared patient bone.

16. The method of claim 15 wherein said prosthetic member forming step comprises forming the attachment surface with at least one groove therein.

17. The method of claim 15 wherein said prosthetic member forming step comprises forming a plurality of spacer pegs to protrude outwardly from the attachment surface.

18. The method of claim 15 wherein said prosthetic member forming step comprises forming the flow restrictor wall to circumscribe the attachment surface.

19. The method of claim 15 wherein said shaping step comprises forming a shallow recess in the prepared patient bone for seated reception of the flow restrictor wall.

20. The method of claim 15 further including the step of pressing a quantity of bone cement into the prepared patient bone at a location adjacent to said attachment surface when said prosthetic member is fitted with the prepared patient bone.

* * * * *